(12) United States Patent
Hastings et al.

(10) Patent No.: US 7,054,677 B2
(45) Date of Patent: May 30, 2006

(54) VENTURI ECG ELECTRODE SYSTEM

(75) Inventors: Mark J. Hastings, Castro Valley, CA (US); Hans-Peter Feucht, Blaustein (DE); Albert Michael Harder, Dornstadt (DE); Donald John Evans, Forest Ranch, CA (US)

(73) Assignee: Venturi Medical Systems, Castro Valley, CA (US)

( * ) Notice: Subject to any disclaimer, the term of this patent is extended or adjusted under 35 U.S.C. 154(b) by 0 days.

(21) Appl. No.: 10/124,616

(22) Filed: Apr. 16, 2002

(65) Prior Publication Data

US 2003/0195408 A1 Oct. 16, 2003

(51) Int. Cl.
*A61B 5/04* (2006.01)

(52) U.S. Cl. ............... 600/509; 600/387; 600/386; 600/388; 600/389; 600/390

(58) Field of Classification Search ............... 600/382, 600/372, 508, 509, 513, 523, 512, 515–517, 600/519, 521, 387, 386
See application file for complete search history.

(56) References Cited

U.S. PATENT DOCUMENTS

| | | | |
|---|---|---|---|
| 2,580,628 A | 1/1952 | Welsh | |
| 3,568,663 A * | 3/1971 | Phipps | 600/387 |
| 3,640,270 A | 2/1972 | Hoffmann | 128/2.1 |
| 3,783,865 A | 1/1974 | Ricketts | 128/128 |
| 4,248,243 A | 2/1981 | Niess et al. | 128/696 |
| 4,556,065 A | 12/1985 | Hoffmann | 128/639 |
| 4,646,747 A | 3/1987 | Lundbäck | 600/387 |
| 4,736,749 A | 4/1988 | Lundbäck | 600/387 |
| 5,092,327 A * | 3/1992 | Tragatschnig | 128/205.13 |
| 5,479,934 A * | 1/1996 | Imran | 600/544 |
| 5,553,612 A | 9/1996 | Lundbäck | 600/387 |
| 5,722,404 A | 3/1998 | Lundbäck | 600/387 |
| 5,724,966 A | 3/1998 | Lundbäck | 600/387 |
| 6,345,192 B1 | 2/2002 | Feucht et al. | 600/387 |
| 6,516,289 B1 * | 2/2003 | David | 600/384 |

FOREIGN PATENT DOCUMENTS

| | | | |
|---|---|---|---|
| DE | 25 48 805 | 10/1975 | 600/387 |
| EP | 0 000 759 | 8/1977 | 600/387 |

* cited by examiner

*Primary Examiner*—Robert L. Nasser
*Assistant Examiner*—Navin Natnithithadha
(74) *Attorney, Agent, or Firm*—Fredrikson & Byron PA (57) ABSTRACT

The present invention provides for an ECG electrode system that includes the use of electrodes adapted to attach to the body via suction. The invention includes a lightweight and compact air pump in combination with air connection hoses, a lightweight air distribution unit, associated electrode tubes, and respective electrodes adapted to be positioned by the Venturi principle, and corresponding electrical leads and recorders/monitors. The electrode leads can each be positioned within respective air connections hoses, e.g., in a manner that is concentric or coaxial with the axis of the connection hoses, in order to both protect the leads themselves and facilitate their positioning.

16 Claims, 10 Drawing Sheets

VENTURI ECG ELECTRODE SYSTEM

FIELD OF THE INVENTION

The present invention generally relates to physiological monitoring electrode systems, also known as electrocardiographs, and to components, including electrodes, for use in such systems.

BACKGROUND OF THE INVENTION

Considerable progress has been made in understanding how electrical signals are generated and used within the body. This progress has led to the ability to monitor various medical conditions by means of transferring electrical energy from the body of a patient. This transfer of electrical energy can be accomplished with electrode systems, which use electrodes to contact the skin of the patient and then transfer the electrical energy from the patient to a recording/monitoring device.

Examples of electrode systems include Computed Tomography imaging ("CT") scans, cardioscopes, electrocardiographs, and electrocardiograms ("ECG"). Unless otherwise indicated, the term "ECG electrode system" will be used herein to represent all or any of these electrode-based devices. Such systems can be used for monitoring the operation of the heart, the respiratory system, and the arterial system.

Generally, a basic ECG electrode system includes the use of at least two electrodes and corresponding electrical lead wires. These lead wires transfer electrical energy from the electrodes, in position upon a patient, to a monitoring apparatus. The electrodes are typically small, round or square, electrically conductive patches, which can be attached to the patient's skin with an adhesive, or with suction, to make electrical contact with the patient's skin. Examples of such electrodes include the Holter Stress Monitoring adhesive electrode manufactured by Lead-Lok, Inc., and Chest Suction Electrodes manufactured by Medesign, Inc.

As is well known, chemical reactions within the body produce electrical current that can be monitored when the electrodes are placed on a patient's skin. Electrical signals generated by the patient's body are transferred from the patient through the electrodes to a monitoring apparatus via the lead wires. The monitoring apparatus then converts the electrical signals from the patient into graphic representations, which a clinician then interprets. Such monitoring apparatuses include the Microscan 2000 manufactured by Advanced Biosensor or the ELI 100/STM ST Monitor manufactured by Mortara.

Presently in the United States, a majority of the ECG electrode systems use some form of adhesive to adhere the electrode to the patient's skin. Examples of such systems include the ZIP TAB™ ECG monitoring electrodes manufactured by Taylor Industries, the Wet Gel/Clear Tape electrodes manufactured by Kendall, Inc, and the 1700 CLEARTRACE™ tape electrode manufactured by ConMed. While these adhesive ECG electrode systems can be useful in performing ECG monitoring, there are significant problems associated with them. First, such a system can result in considerable discomfort for the patient. Typically the area where the electrode is to be placed must first be shaven to ensure proper electrical connection. This process not only takes time, which adds to the expense of the overall procedure, but is also uncomfortable for the patient and increases the chance of injury and infection. Further, there are considerable costs associated with the use of these disposable electrodes, including the cost of the electrodes themselves, plus delivery costs, storage costs, and disposal costs.

Second, most adhesive ECG system electrodes are manufactured to be disposable, having some or most of their component parts in plastic form in order to permit the electrodes to be discarded after use, thereby resulting in additional waste and burden on the environment. Another drawback associated with conventional adhesive ECG systems is the loss of adhesiveness when the electrode is removed from the skin. For example, if a clinician needs to move an already adhered electrode in order to obtain a better patient signal, the chances of the electrode being effectively re-adhered to the patient are greatly reduced. This is because the electrode's ability to adhere is reduced each time the electrode is removed from the patient's skin. Yet another drawback is the risk that the patient might be allergic to the adhesive itself. Finally, there is the time consuming process of cleaning the adhesive off of the patient's skin after the ECG process is completed.

To address these problems, a handful of ECG electrode systems rely on suction, rather than adhesives, to attach the electrode to the patient's skin. The suction is created with a vacuum inside of the suction cups, which house the electrodes. In use, the electrodes can be effectively adhered to the patient's skin by placing the suction cup on the patient's skin. As the vacuum is created, the low pressure that results causes the patient's skin to rise up slightly toward, and into contact with, the electrode. Once attached in this fashion, the patient's electrical signals can travel from the electrode through a lead wire to a suitable monitoring station.

Early types of ECG suction electrode systems, such as that described in U.S. Pat. No. 2,580,628 and similarly manufactured by Medesign, Inc., employ an electrode in the form of small hemispheres made out of steel with a small rubber ball at the top end. Although quite simple in operation, such electrodes suffered from the inconsistent vacuum produced.

To resolve these drawbacks manufacturers began using pumps connected to the electrodes through air hoses to create the vacuum inside of the suction cup. Conventional pumps create the vacuum within an electrode by sucking air toward the pump, thereby creating negative pressure inside the suction cup. The negative pressure, in turn, pulls the cup toward the skin of the patient thus engaging the electrode with the skin. However, ECG electrode system must typically use low-suction vacuum pumps or reaction pumps, and thereby avoid the use of large suction, which could produce a high risk of a hematoma, leading to a variety of related problems. The use of low suction, however, increases the chance that electrodes will fall off in the course of use. This meant the ECG system operator would have to spend valuable time re-adhering the electrodes and this extra time produces extra labor costs.

In turn, ECG electrode systems such as those described in U.S. Pat. Nos. 3,640,270 and 4,556,065 began using more powerful pumps to reduce the amount of time it takes to secure the electrodes to the skin. However, such systems increased the risk that the vacuum might become too strong and thus increase the risk of hematomas. To prevent this from happening, the operator must manually adjust the pump to maintain the appropriate vacuum, in addition to also monitoring the ECG data itself.

Another disadvantage of the pump-based ECG systems, as described above, are the difficulties relating to the removal and re-adherence of the electrodes. For example, if an operator desires to move a single electrode after suction has been created, the operator must first turn off the pump; then wait for the suction to dissipate; move the electrode to its desired location; and finally reinitiate the suction process all over again. A further disadvantage, of both ECG pump systems described above, is that the air flowing towards the pump can carry contamination into the pump system, such as sweat, hair, and electrode paste. Although filters can be used, the risk of contamination of the system and infection of the patient is not entirely avoided. Further, the contamination of the pump system requires the system to be cleaned frequently and makes the cleanup of the system extremely difficult. The problems surrounding the cleanup of the system are also compounded by associated labor costs.

The above-described ECG electrode systems also tend to have drawbacks associated with their design. Because of their suction pump construction, the US Food and Drug Administration restricts the use of such systems in the United States due to the high possibility of cross-contamination. These systems are also limited due to their bulkiness. The fact that the systems must house pumps to generate the suction causes them to be quite heavy. Further, the acquisition modules or distribution boxes which route the signals to the recorders/monitors can be large and heavy due to the electronics on board which digitize the signals coming form the patient before being routed to the ECG recorder. This bulkiness causes the systems to be heavy and immobile and therefore reserved for use in one location. Finally, typical ECG system lead wires are $\frac{1}{16}$ of an inch in diameter. These lead wires are expensive and reputed to break quite often due to their thin design and repeated movement throughout an ECG procedure.

What is clearly needed are ECG systems that provide an improved combination of various features, including physical characteristics (such as weight and compactness), cost, clinical efficacy, environmental protection, and patient comfort.

SUMMARY OF THE INVENTION

The present invention provides an improved ECG electrode system comprising:

(a) an air pump of suitable weight and compactness for providing positively pressurized air through an exit orifice, (b) a flexible air connection hose of sufficient length to extend from the air pump to a patient and having first and second ends, the first end of the hose being operably and detachably connected, or connectable, to the exit orifice of the pump, (c) an air distribution unit of sufficient weight and size and comprising a plurality of exit apertures and associated connectors, and at least one intake aperture and associated connector, the intake connector being detachably connected, or connectable, to the second end of the connection hose in order to controllably route pressurized air received from the pump, through the connection hose, and to the exit apertures, (d) a plurality of electrode tubes each comprising first and second ends, the first ends of each being operably and detachably connected, or connectable, to a corresponding distribution unit exit aperture, (e) a plurality of Venturi electrodes, each being operably and detachably connected, or connectable, to the second ends of the electrode tubes receiving compressed air from the electrode tubes, and (f) a plurality of electrical leads adapted to sense and relay electrical charges occurring within the body by means of a centralized universal electrical connector, which is connectively compatible with an ECG recorder and/or monitor.

In a particularly preferred embodiment, the electrode leads are each positioned within respective air connections hoses, e.g., in a manner that is concentric or coaxial with the axis of the connection hoses, in order to both protect the leads themselves and facilitate their positioning.

The electrodes for use in a system of this invention are attached by means of a vacuum. The vacuum draws the patient's skin into contact with the electrode and holds it there with a constant force while the ECG recording is taken. The stream of air creating the vacuum is supplied to the each electrode housing by flexible tubing connected to a small DC-powered air pump. The ECG lead wires are preferably built into the air pressure tubing connected to each electrode. This cable assembly plugs into the connection box that, in turn, is connected to the ECG recorder and the air pressure pump. When the ECG exam is completed, the electrodes are released by turning off the air pressure pump. When airflow stops, the vacuum inside each electrode subsides and the electrodes fall off the patient within one second. This is in stark contrast to removing the adhesive electrodes, which can take anywhere from 10 to 180 seconds depending on the amount of electrodes and the patient being examined.

As compared with conventional "Welsh Cup" ECG electrodes, the air stream-powered vacuum of the present invention maintains constant, intimate contact between the electrode and the skin that is equal in quality or better than the contact that is possible with conductive creams, gels, and the adhesives used with disposable electrodes. The constant suction maintains a seal around surface irregularities, including hair. This allows optimal skin continuity to be maintained without shaving contact patches, where this would be customary and necessary practice with conventional electrodes.

No conductivity creams or gels are required with such electrodes, both because they are generally not needed, and because they can tend to clog the air jet passages. A water-based conductivity-enhancing fluid may optionally be used with such electrodes, where indicated. If an electrode needs to be repositioned, its suction can be neutralized temporarily by holding a finger over its air exit port. This causes the air stream to spill into the suction chamber, lifting the electrode off the skin. Eliminating time spent shaving, re-attaching slipped electrodes, and assisting patients with clean up after measurement significantly reduces the time needed to examine each patient. These timesavings, along with the elimination of expendable supplies used for connecting patients and reduction of lead wire replacement costs, contribute to notable savings for ECG operations.

In its preferred embodiment, a system according to the present invention provides an optimal combination of such features and functions, including those that arise: 1) in the manufacture, packaging, and transport of the system, 2) in the course of setting up and using the system, and/or 3) in related matters such as ongoing maintenance.

With respect to item 1) above, the system provides improved portability and ease of maintenance, due at least in part to its lightweight components and modular construction. The ECG electrode system of the present invention preferably has a pump unit, a charger unit, a distribution unit, a plurality of electrodes and a plurality of electrode tubes, a connection hose, a combination plug and recorder/monitor connector, and a jack box (e.g., connector hub) necessary when using digital ECG recorders/monitors.

The pump unit, in turn, preferably includes a pump, batteries, a control unit preferably having a plurality of charging indicators, a remote jack, an air aperture, and a charger jack. The pump unit is preferably comprised of a compact compressor pump. With a compact pump the ECG system of the present invention becomes lighter. This is because in some ECG suction systems the pump can be both heavy and large and thus the housing for the unit can be large. This can make the housing difficult to move from place to place.

Preferably, batteries are provided and used to supply power to the pump. It is preferred to have batteries that can provide a long electrical life. Preferably the batteries are of a sealed lead acid design, for its durability during repeated periods of charging and discharging. Further, the batteries preferably have a long electrical life and can typically withstand between 40 to 50 examinations before the batteries are in need of recharging.

The control unit is responsible for providing power from the batteries to the pump unit upon activation by the operator of the remote switch. Upon remote switch activation, the control unit preferably provides power to the pump and charging indicators. A printed circuit board has the necessary circuitry to receive inputs from the batteries, battery charger, and the remote switch. The printed circuit board circuitry then uses this information to determine whether the improved ECG system is on or off, whether the improved ECG system is charging or not, and what indicators should be lit to tell the operator how much charge is left.

The charger unit preferably has a charger plug and a wall plug. The charger unit is used to make the ECG system of the present invention more portable, for example, in order to perform an ECG on a patient in a location without a wall outlet or any other outside power source, such as a generator.

The distribution box preferably receives the electrode hose or hoses. The distribution box is made of a lightweight construction, preferably a durable plastic, to improve its portability. Unlike typical ECG systems, the distribution box will not typically have any electronics onboard which process the patient's electric signals. This helps ensure the boxes' compact construction. Further, the distribution box has a remote activation switch, which allows the operator to operate the improved ECG system several feet away from the pump unit.

With respect to item 2) above, and particularly in view of the electrodes and electrode tubes, the system provides an improved combination of features, such as ease of fixation to the body, tenacity, contamination prevention, and release characteristics, due at least in part to attachment based on the Venturi principle. Contamination prevention is improved, for instance, by having the air pushed away from the pump and towards the electrodes thus preventing any liquid, skin particles, hairs, dirt, etc. from being sucked into the system. The current system also provides improved control and reproducibility in the course of its use, e.g., permitting both constant and controllable air pressure. Such control can be achieved both by operator controls, e.g., pump controls, as well as by careful selection of nozzle diameters of the Venturi tubes themselves. Adhesion of the electrodes is both easier and quicker for the operator, and typically more effective and comfortable for the patient. Attachment can typically be achieved without the need to shave the body portion, and release of the electrodes can be quickly and easily accomplished by controlling (typically stopping) the flow of pressurized air in an appropriate manner.

Both the electrode tube and connection hoses have a strong outer sheath built from a flexible material such as rubber or polymeric material (e.g., polyvinylchloride ("PVC")). This allows for ease of handling and allows for the tubes and hose to navigate around corners or obstacles. Preferably, the electrode tubes and connection hose are constructed so that all the lead wires traverse a lumen within the sheath. With this construction the electrical wires are kept out of the operator's way and therefore do not become a hazard to the operator, or become detached by accident. Further, the electrical wires are preferably of a thicker diameter, to reduce the possibility of breakage through repeated use.

Preferably the connection hose is detachably connected to a combination plug, e.g., in the form of a 15-pin mini-DSub connection. From here, an outside connection cable can be plugged into D-Sub connector at the combination plug and the other end plugged into any analog ECG recorder or monitor. The DSub connection allows for any analog recorder/monitor to be directly plugged in the ECG electrode system of the present invention. Further, a jack box can be connected to the DSub connector. The jack box is then connected and routes the various signals coming from the electrodes to several or one analog to digital converters, which then feed the digital signal to any digital ECG recorder or monitor. The jack box can also have the analog to digital converters onboard in which case the jack box then routes the digital signal to any digital ECG recorder or monitor. Further, the jack box can be connected to an acquisition box of a standard ECG system, which then digitizes the analog signal and then routes the signal to any digital ECG recorder or monitor.

With respect to item 3) above, the system provides low maintenance, and less waste, as compared to most conventional systems. For instance, as compared to conventional systems in which the electrodes, lead wires, electrode tubes, and the filter must be continually cleaned and maintained, in a system of the present invention typically only the electrodes themselves require periodic cleaning.

The present invention can also be used for performing ECG stress testing, for instance on ergometers and/or treadmills, as well as for "resting" ECGs. Typically, stress testing requires costly disposable adhesives based electrodes that are larger in size and have more conductive material fixed to their surface, as compared to smaller resting ECG electrodes. In a stress testing mode, the skin surfaces used for electrode placement are typically "shaved and sanded" with a razor and sandpaper (used to actually abrade the skin) in order to provide an improved conductive surface area for attachment of the adhesive electrode. Typically "skin prep" is required for the pre-cordial leads, V1 & V2 electrodes, in a process that can take any where from 4 to 15 minutes per electrode. Additionally, shaving of the skin exposes the patient to increased risk of infection from razors and or other microbes present in the examination field.

The present invention offers improved speed, safety, and patient comfort while delivering equivalent to improved performance, e.g., in terms of waveform accuracy, for the stress testing diagnostic procedure. The present invention endeavors to improved the speed of electrode application to the skin surface while simultaneously reducing preparation time. For optimal ECG accuracy, electrodes frequently need to be repositioned or moved. Using the Venturi based electrode of this invention, the stress testing operator can perform this maneuver in seconds, as compared to multiple minutes for a disposable adhesive electrode. Furthermore the Venturi electrode can be placed and fixed to the skin of even hairy individuals without the necessity of shaving, thus reducing the possibility of infection to the patient.

For use in such an embodiment, the system of this invention can include, for instance, a suitable vest for use as a secondary electrode stabilization component. Such a vest can be prepared using any suitable material in order to permit it to be both lightweight and comfortable, e.g., a mesh type material having over 90%, or even over 95% open space. One of the major benefits of a system of this type is the reduction of preparation time spent on the patient. Preparation time can be reduced from 10 to 15 minutes for adhesive-based disposable electrodes, only a few seconds for the Venturi based system. Also, as a patient sweats during a typical stress test, disposable adhesive based electrodes have been known to fall off and fail (due to sweat accumulation under the electrode). This problem is alleviated, if not avoided entirely, using the present system, because as skin surface moisture increases, electrical resistance decreases dramatically, and conductivity improves. Additionally, the Venturi based electrodes are non-disposable, which not only helps keep the environment cleaner but also delivers an improved cost-benefit ratio, which can contribute to lower overall healthcare costs. By comparison, adhesive-based disposable electrodes can cost anywhere from $1.25 to $3.50 (a stress test requires a minimum of 10 electrodes) depending on the volume of total tests performed the medical practitioner.

DESCRIPTION OF THE PREFERRED EMBODIMENT

To assist in an understanding of the invention, a preferred embodiment or embodiments will now be described in detail. Reference will be frequently taken to the Figures, which are summarized above. Reference numerals will be used to indicate certain parts and locations in the Figures. The same reference numerals will be used to indicate the same parts or locations throughout the Figures unless otherwise indicated.

Figure 1:
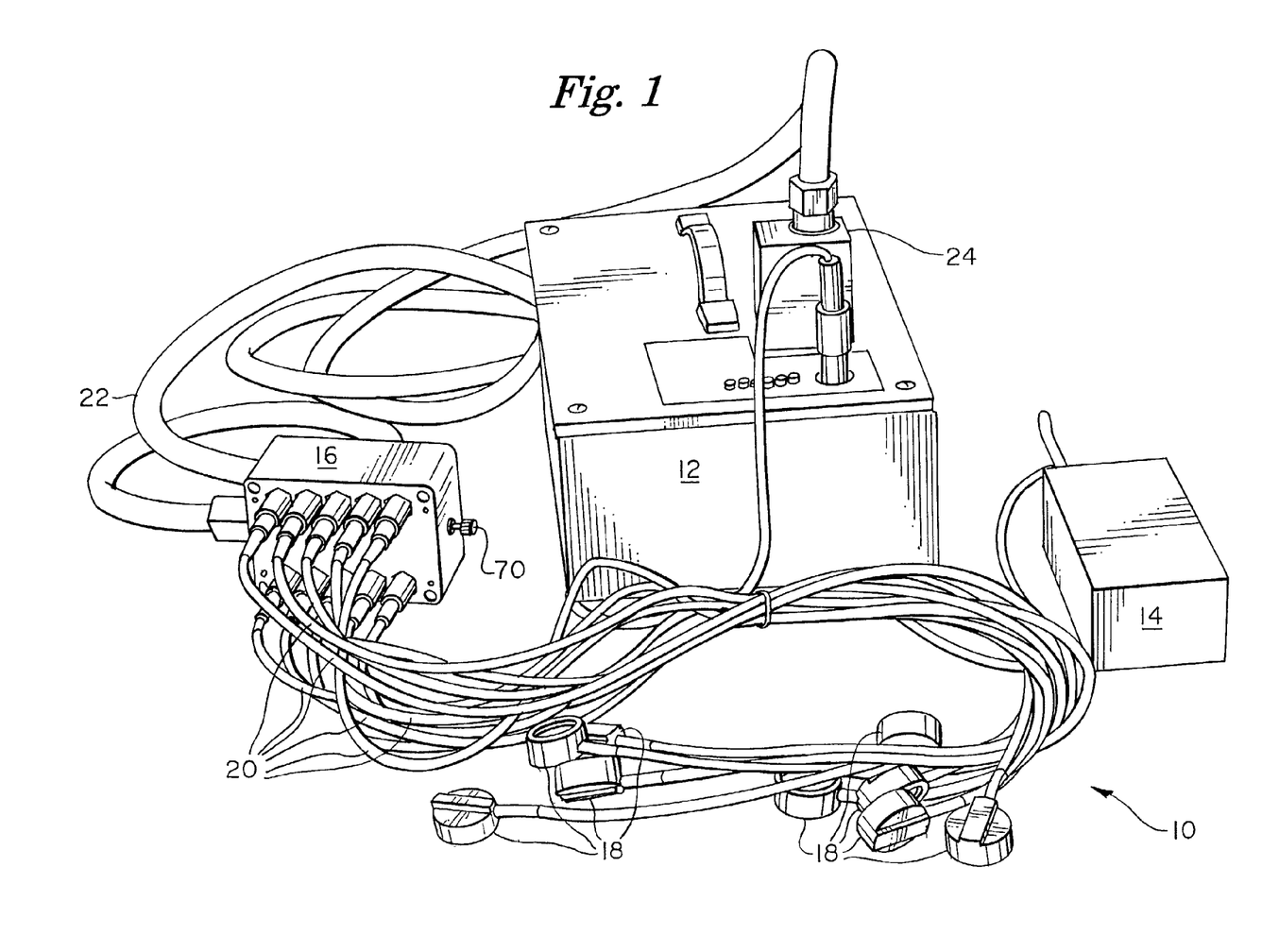
FIG. 1 is a front perspective view of an embodiment of an ECG system of the present invention.
Figure 2:
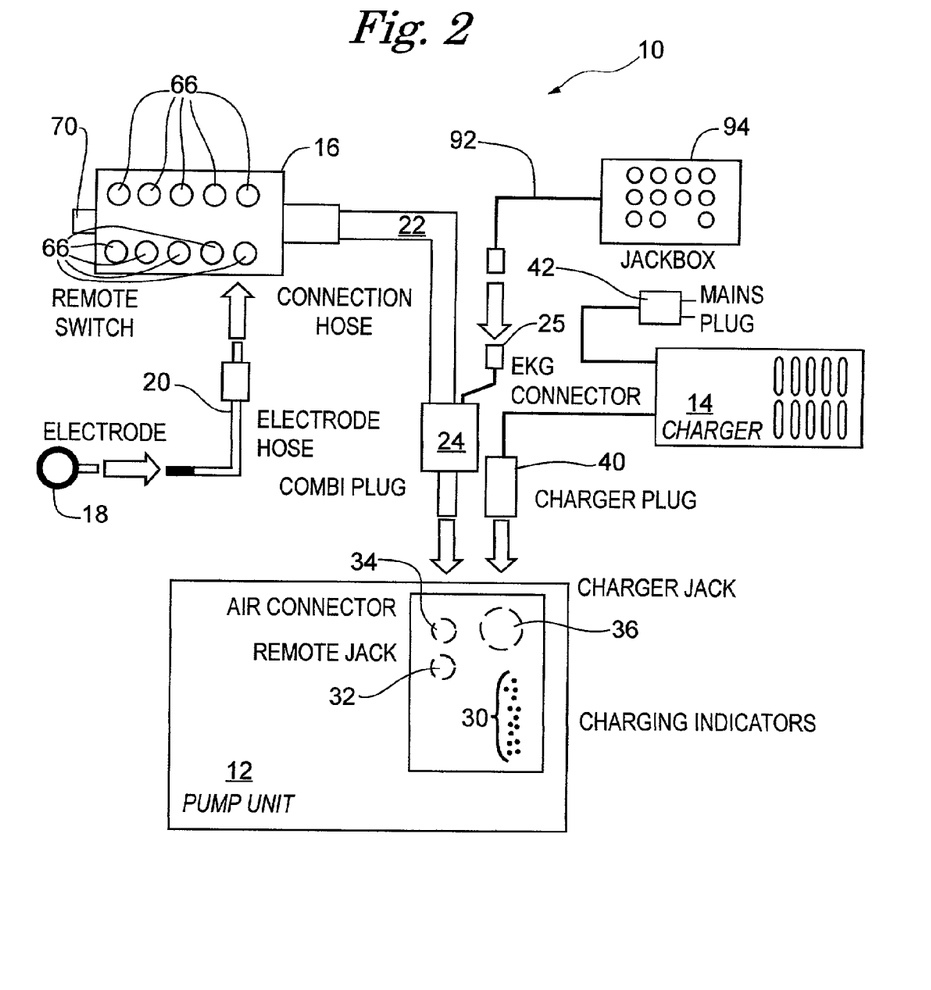
FIG. 2 is an exploded view showing the respective component parts of a system according to FIG. 1.

With respect to FIGS. 1 and 2, an improved ECG electrode system 10 is shown having a pump unit 12, a charger unit 14, a distribution unit 16, a plurality of electrodes 18, a plurality of electrode tubes 20, a connection hose 22, a combination plug 24 and recorder/monitor connector 25, and a jack box 94, discussed in more detail herein. The following discussion will describe each part in detail, including how the individual parts interact during operation.

Figure 3:
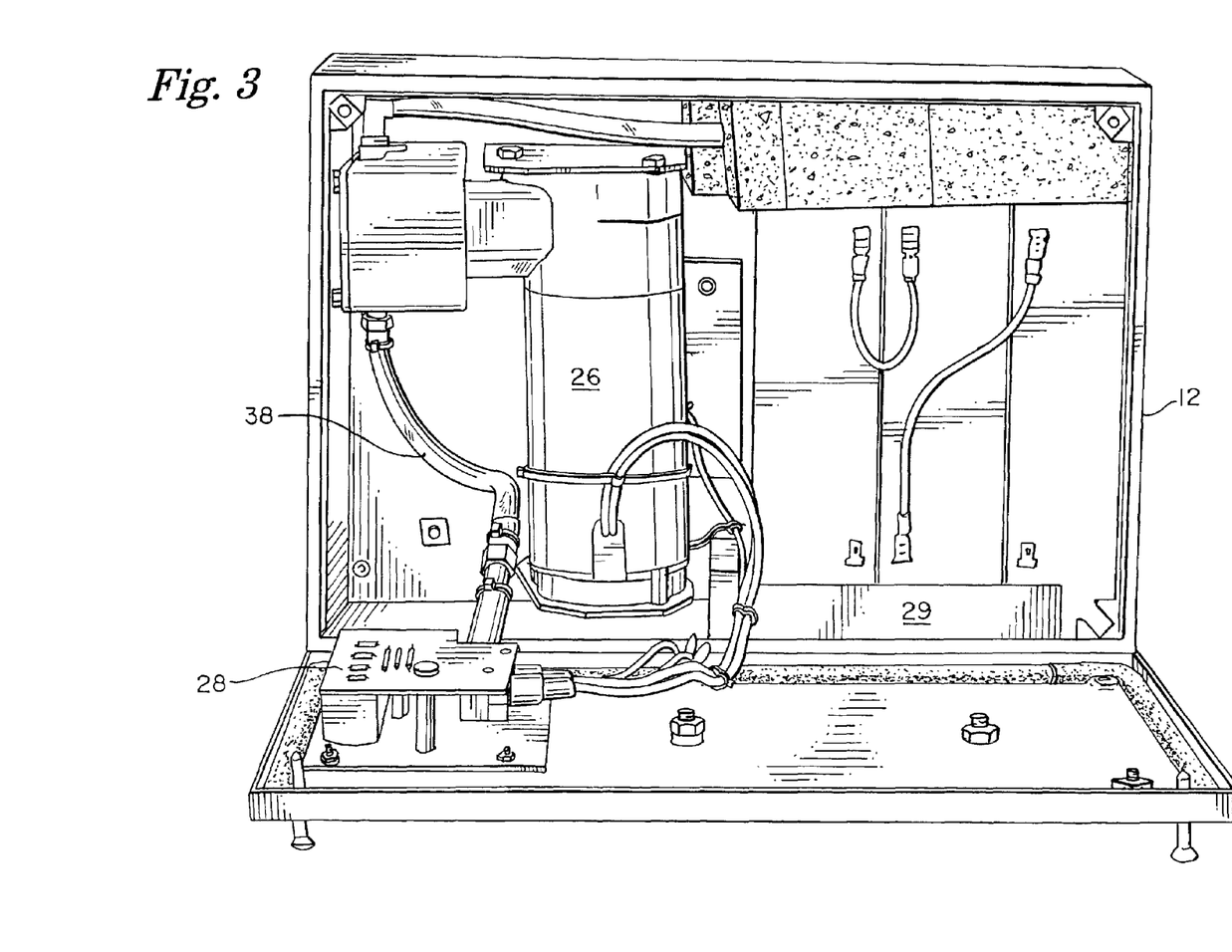
FIG. 3 is a front view of the pump unit opened to show an embodiment of the pump unit of the present invention.

With respect to FIGS. 2 and 3, an improved pump unit 12 is shown having a pump 26, batteries 29, a control unit 28 having a plurality of charging indicators 30, a remote jack 32, an air aperture 34, and a charger jack 36.

Pump 26 can be any suitable air compressor, such as an oil-less reciprocating compressor, a gas compressor, or reciprocating compressor designed to supply a vacuum of approximately 150 to 200 mbars, although the optimum operating condition is an electrode vacuum of between 120 and 180 mbars to lessen the risk of hematoma. Pump 26 is preferably a compact Thomas compressor pump, model number 315CDC40/24, manufactured by Thomas Compressors and Vacuum Pumps, Sheboygan, WI 53802. With a compact pump, ECG system 10 becomes lighter. With further reference to FIG. 3, pump 26 is connected to control unit 28 with air hose 38 and supplies compressed air from pump 26 to air connector 34 when system 10 is operating.

Batteries 29 can be any suitable batteries such as alkaline batteries, nickel-cadmium, or lithium batteries, which can supply approximately 12–25VDC. Batteries 29 are preferably comprised of (3) 6V/12 Ah batteries made of a sealed lead acid design, and provide suitable internal voltage (e.g., 12–18 VDC) to ECG electrode system 10; though other batteries are contemplated for use as well, without straying from the sprit of the invention. However, it is preferred to have batteries that can provide a long electrical life. The sealed lead acid design is chosen for its durability during repeated periods of charging and discharging. Batteries 29 provide power to pump unit 12 and in particular to pump 26 and control unit 28. Further, batteries 29 have a long electrical life and can typically withstand between 40–50 examinations before the batteries are in need of recharging.

Control unit 28 preferably includes a printed circuit board which houses the appropriate circuitry, such as memory and a microprocessor or microcontroller or specially manufactured integrated circuit, which allows for various inputs and outputs. Control unit 28 is responsible for providing power from batteries 29 to pump unit 12 upon activation by the operator of remote switch 70, discussed below. Upon remote switch activation, control unit 28 provides power to pump 26 and charging indicators 30. The printed circuit board is responsible for providing power to the proper indicators 30 during charging and use. The printed circuit board receives inputs from batteries 29, battery charger 14, and remote switch 70. The printed circuit board then determines whether system 10 is on or off, whether system 10 is charging or not, and what indicators 30 should be lit to tell the operator how much charge is left.

Figure 4:
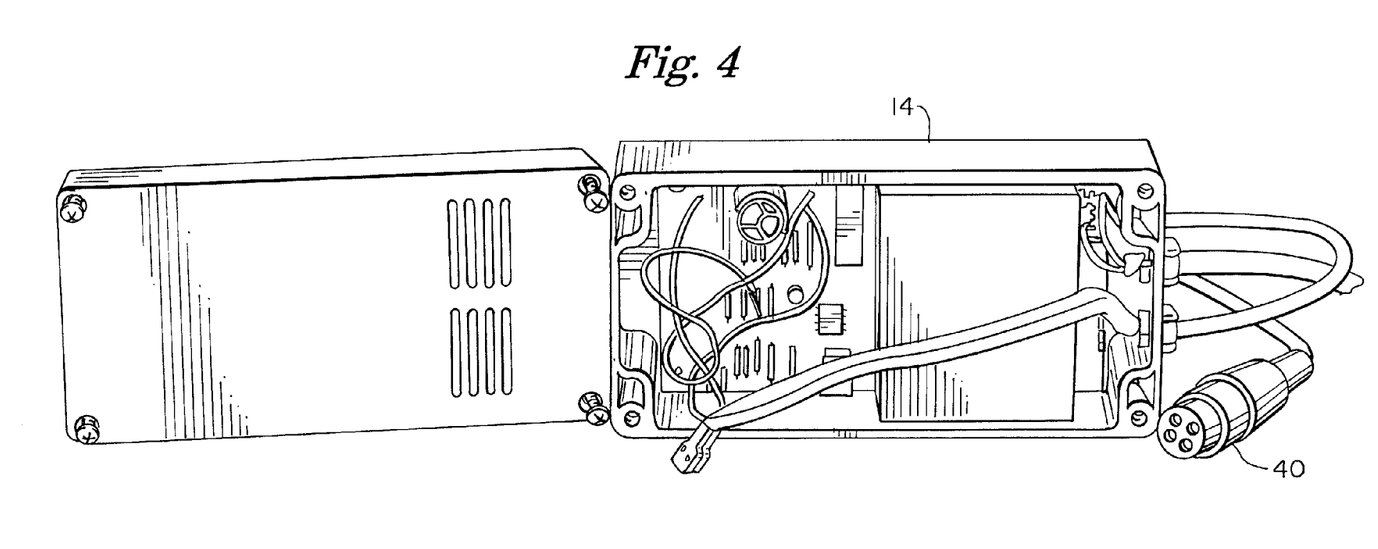
FIG. 4 is a front view of the charger unit opened to show an embodiment of the battery charger of FIG. 1.

With respect to FIGS. 2 and 4, charger unit 14 is shown having a charger plug 40, and a wall plug 42. Charger unit 14 can be any suitable charging unit. For example, the battery charger can be any unit that converts 115V, 60 Hz, and 30 VA to appropriate charging voltage (e.g., about 12VDC to about 22VDC). The embodiment in FIGS. 3 and 4 specifically shows a charger unit which connects to a standard wall outlet, however, it is contemplated that charger unit 14 can utilize any power source for charging purposes other than a standard wall outlet. It is further contemplated that pump unit 12 can plug directly into a standard wall outlet.

However, in a preferred embodiment system 10 uses batteries 29 and battery charger 14 in order to make the unit more portable. Preferably, before the system's initial use, batteries 29 are charged for approximately 6 hours to ensure a proper charge. However, after the initial charge, the charging time is considerably reduced to approximately 2 hours. Therefore, the amount of downtime for the unit is decreased and it can quickly be used again.

As shown, the printed circuit board will sound a 10 second audible sound, such as a beep, and the <25% indicator lamp will activate each time batteries 29 is in need of a recharge. The audible sound and indicator lamp will also activate each time the unit is turned on and system 10 requires charging. However, system 10 can perform more ECGs in this condition, but the reliability of the electrode suction, and thus the accuracy of the ECG data, will be reduced with every examination after the initial indication of a need for charging.

Figure 5:
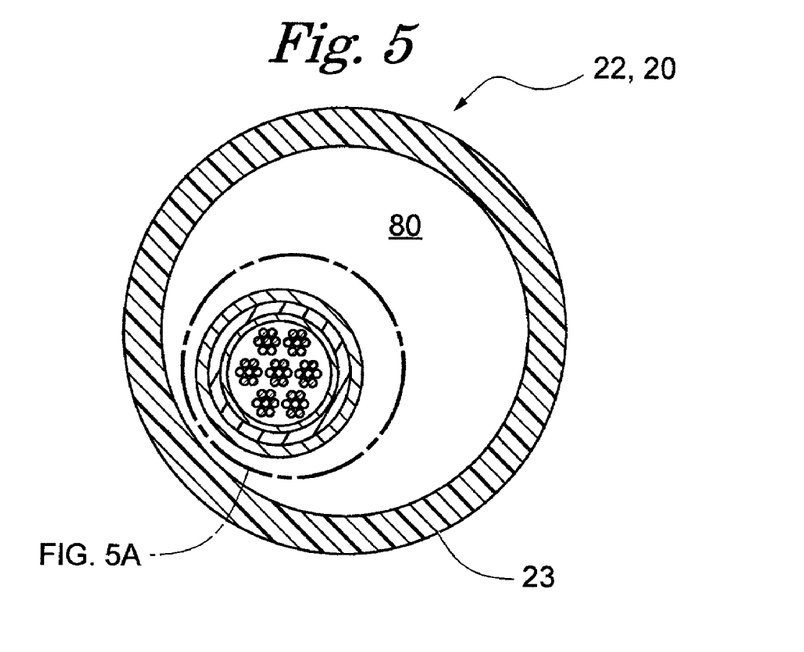
FIG. 5 is a cross sectional view of a preferred embodiment of the electrode tubes and connection hose.
Figure 5A:
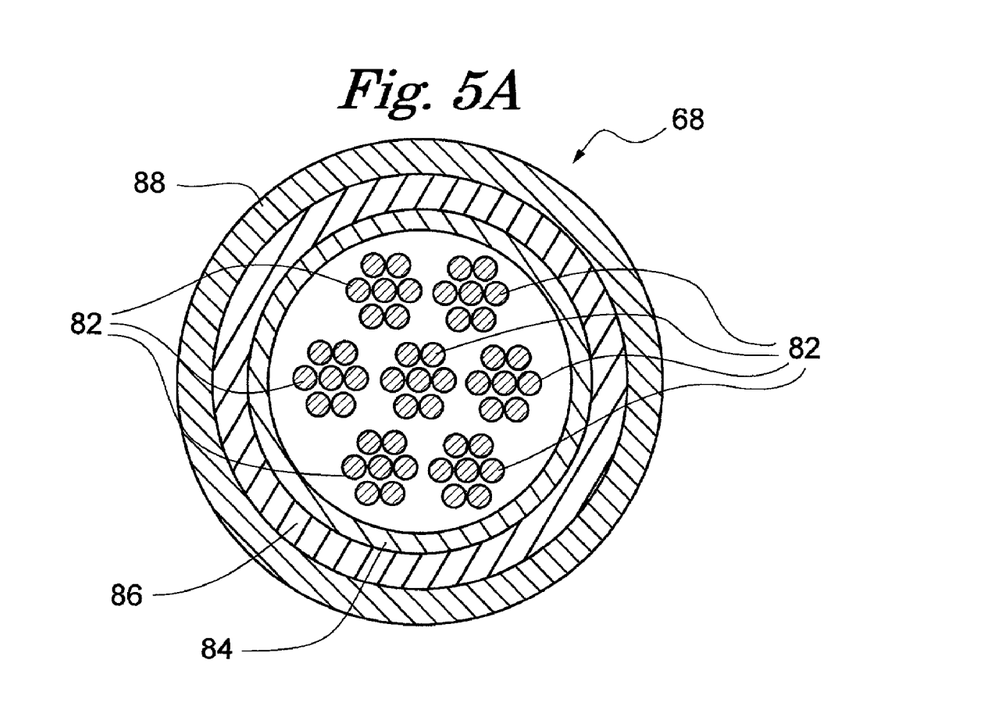

With reference to FIG. 2, distribution box 16 can be any suitable distribution box or acquisition module commonly used in ECG electrode systems. Distribution box 16 preferably has 10 apertures 66 which can receive corresponding electrode hose or hoses 20. Distribution box 16 is made of a lightweight construction, preferably a durable plastic, to make it portable. Unlike typical ECG systems, box 16 does not have any electronics onboard which convert the patient's electric signals from analog to digital. Distribution box 16 has a remote activation switch 70. When the operator activates system 10 from remote switch 70 an electrical signal is sent down connection wires 68 located inside connection hose 22 into pump unit 12 to control unit 28 (FIG. 5). Control unit 28 then relays power from batteries 29 to pump 26, which begins operating and pumping air throughout system 10. The fact that no electronics are typically required to be on board not only results in light weight and compactness, but also in nearly universal utility with all recorders. All recorders have to deal with 1 mV analog signals at the very front end, and it is at that position where the present device can be inserted into the signal path.

With respect to FIG. 5, improved electrode tube 20 and connection hose 22 can be any suitable hose or tubes used for the delivery of air pressure. Both tube 20 and hose 22 preferably are constructed to withstand air pressures up to about 500-lbs/square foot. Further, both tube and hose 22 preferably have a strong outer sheath 23 built from a flexible material such as rubber or poly(vinylchloride) (PVC). This allows for ease of handling of tube 20 and hose 22 and allows for the hose to navigate around corners or obstacles. Preferably, tube 20 and hose 22 are constructed so that all lead wires traverse inside of sheath 23.

Due to the long flexible connection hose 22 connecting pump unit 12 and distribution box 16, system 10 can be installed on a cart, such as the mobile 20TX treatment cart distributed by Total Pharmacy Supply, Inc. in Arlington, Tex. Thus, pump unit 12 can be placed anywhere on the cart, for example, on the lower shelf of the cart. The flexibility of connection hose 22 allows for distribution box 16 to be placed onto or beside the patient during the examination. This eliminates several electrode hoses from becoming tripping hazards or from becoming disconnected from the patient because the electrode hoses are now local to the patient. Therefore the risk of injury or disconnection is significantly reduced.

As stated above, sheath 23 is preferably made of a flexible material such as a soft PVC or rubber. Hoses 20 and 22 preferably provide an inner diameter that leaves an opening 80 large enough for the proper amount of pressurized air to reach distribution unit 16 and electrode 18. Further, traversing the inside diameter of hoses 20 and 22 are lead wires 64 and connection wires 68. Wires 64 and 68 can be of any type of electrical construction, however, in a preferred embodiment wires 64 and 68 are constructed with a conductor 82 preferably made out of copper with a central conductor made from stainless steel. Surrounding conductor 82 is a layer of Polytetrafluoroethylene ("PTFE") or other suitable insulation 84. Outside of PTFE layer 84 is a thin layer of silver plated copper shielding 86. Shielding 86 prevents any outside electronic disturbance from penetrating and corrupting any data traversing along conductor 84. Finally, another outer PTFE insulation layer 88 covers shielding layer 86 to protect shielding layer 86.

Electrode 18 can be any suitable Venturi type electrode that generally has a cup-shaped housing of non-metallic material. The cup-shaped housing preferably has a mouth bounded by a tissue-engaging rim. The housing contains an electrode, which is recessed within the rim but accessible by way of its mouth in order to make contact with the skin of the patient. The electrode preferably is plated with a mixture of silver and one or more silver salts such as silver chloride, silver bromide, silver rhodamine, or silver cyanide but can be plated with any electrically conductive metal.

Figure 6:
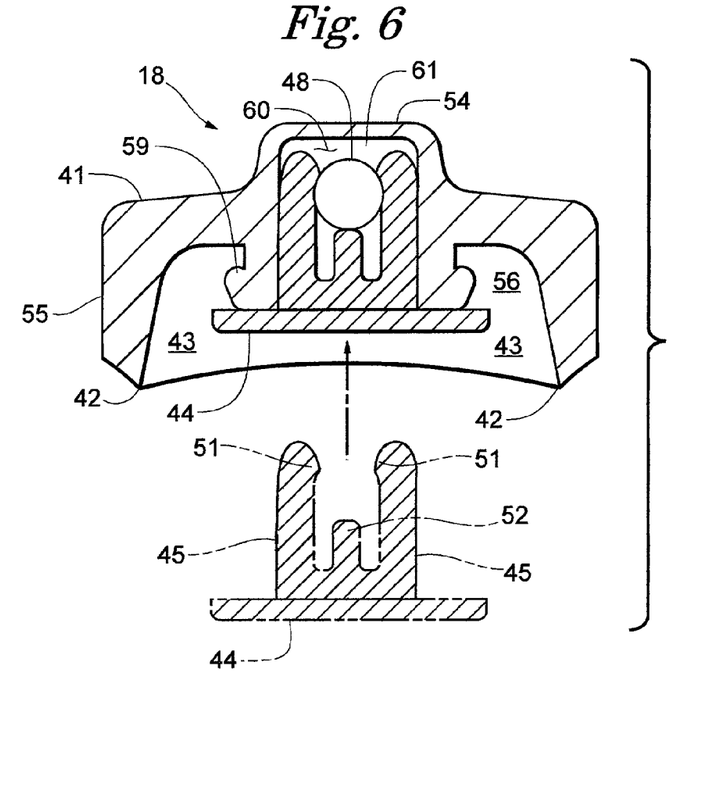
FIG. 6 is a cross sectional front view of a preferred embodiment of a suction electrode suitable for use in a system of this invention.
Figure 7:
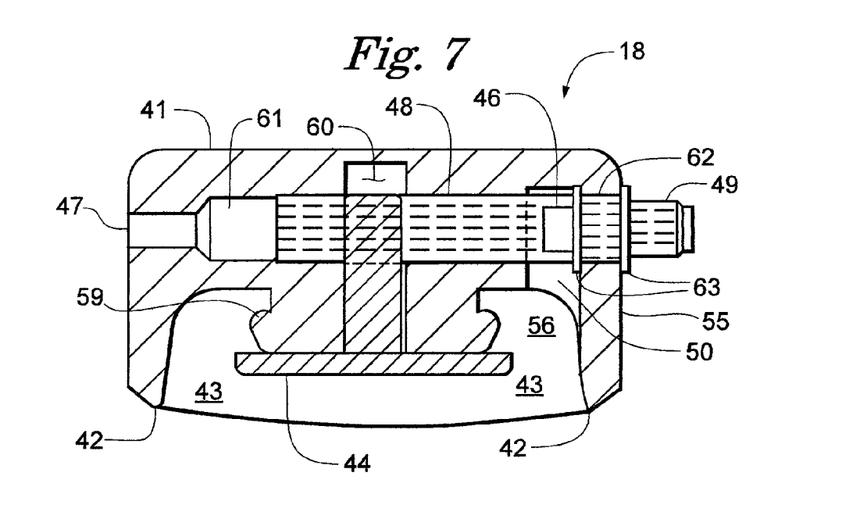
FIG. 7 is a cross sectional profile view of a preferred embodiment of the suction electrode of FIG. 6.
Figure 8:
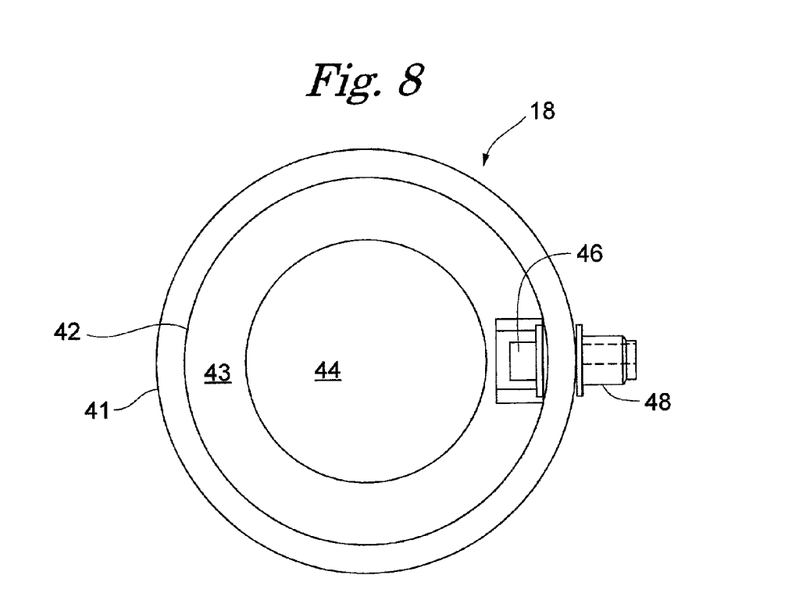
FIG. 8 is a bottom view of the suction electrode of FIG. 6.

Now with respect to FIGS. 6, 7, and 8, a preferred embodiment of electrode 18 is shown. Electrode 18 includes a cup-shaped housing 41 of a one-piece rubbery material. Preferably the material is flexible, such as silicon, and is able to make a good seal when in contact with the patient's skin. Housing 41 includes an end-wall 54 connected across an annular sidewall 55. Sidewall 55 has a free terminal edge defining a rim 42, which defines or bounds an open mouth 43 into a main recess 56 of housing 41. During operation a low-pressure vacuum created by pump 26 causes organic tissue to be sucked through mouth 43 and enter recess 56 and then engage contact plate 44 of electrode 18, see FIG. 6.

Rim 42 provides for engaging tissue and creating a seal there against when the pressure vacuum is created. As stated above, the sealing is easily accomplished if the housing material is rubbery or flexible in nature. Within housing 41 is a central material extension 59 depending from the underside of end-wall 54. Extension 59 defines a leg well 60 exposing therein a portion of the Venturi tube 48 for the legs of contact plate 44 to snap onto or damp about, as can be ascertained from FIG. 6. The rubbery housing material defining the leg well 60 is sized to engage electrode legs 45 on multiple sides thereof and to thereby aid in holding contact plate 44 securely in place. Housing 41 includes a transverse through passage 61 in which Venturi tube 48 resides. Generally passage 61 is smaller in diameter than the exterior of Venturi tube 48 and thereby the material defining the passage 61 grips and frictionally holds Venturi tube 48 securely in place after it has been placed into passage 61. Further, the tight fitting rubbery material of housing 41 also seals in the appropriate areas against Venturi tube 48.

Through passage 61 is defined or bounded by the rubbery material of housing 41, and includes an opening 50 to through passage 61 aligned with suction port 46 of Venturi tube 48. Therefore, a vacuum can be created in main recess 56 of housing 41. An output port 47 to through passage 61 is aligned with the gas output end of Venturi tube 48, which allows the pressurized gas distributed from pump 26, to exhaust to the exterior of housing 41. Thus, all contaminates are pushed out of ECG electrode system 10. Through passage 61 further includes an opening 62 for the introduction of pressurized gas into Venturi tube 48 at threaded end 49. Threaded end 49 of Venturi tube 48 is exposed for connection to electrode hose 20 and an output lead wire 64. In a preferred embodiment, contact plate 44 is positioned in housing 41 and at least in part exposed in recess 56 through mouth 43.

Electrode 18 comprises contact plate 44 with a first side facing housing mouth 43 and providing a surface for engaging organic tissue. The first side of contact plate 44 is shown circular in FIG. 8, and is generally flat and smooth so as to not be abrasive to skin. For further comfort against the skin (tissue) the lower corner is a rounded-over or beveled (see FIG. 6) so to be smooth against the skin. An opposite and a second side of electrode contact plate 44 includes a pair of extensions or legs 45 and a limiter post 52 centered between legs 45. Legs 45 and limiter post 52 point away from the backside of contact plate 44 and are comprised of plastic. The plastics from which contact plate 44 are molded can be acrylonitrile-butadiene-styrene ("ABS"), although other plastics can be utilized. Contact plate 44 is an inexpensive one-piece molded plastic base or substrate, which is, coated with a thin and thus inexpensive exterior layer of silver/silver chloride AgAgCl so as to be electrically conductive on the exterior surface of contact plate 44. Silver/silver chloride in a thickness of 0.004 inches functions well, but the thickness can be varied widely within the scope of the invention. A coating of low resistance electrically conductive material such as a silver based material other than silver/silver chloride or equivalent can be used on the exterior of the electrode within the scope of the invention although the silver/silver chloride proves more durable.

The legs 45 of electrode 18 are resilient because of the strength of the plastic and shape thereof, and are spaced apart from one another to receive Venturi tube 48 in-between and snap fit or clamp there against to physically and electrically connect with Venturi tube 48. The normal or non-loaded spacing between legs 45 in the area where tube 48 is clamped is less than the diameter or width of the Venturi tube 48 so that the legs 45 are continuously trying to move inward when tube 48 is clamped, thereby clamping pressure and thus good contact is maintained between legs 45 and Venturi tube 48. Each leg 45 includes, what is in effect, a curved indentation 51 in which Venturi tube 48 resides. Indention 51 as shown in FIG. 6, is defined by the leg end curving inward to form a hook or prong like structure overhanging the top of tube 48, and thereby increases the stability of the connection as well as increasing the surface area contact between legs 45 and Venturi tube 48 for lower electrical resistance at the contact points.

Limit or limiter post 52 extends up to contact the underside of Venturi tube 48 and aid in supporting tube 48 and legs 45 properly positioned to one another. The terminal end of center material extension 59 of housing 41 abuts the backside of contact plate 44 and thereby provides further position stabilizing relative to Venturi tube 48. Legs 45 fit snugly into leg well 60 and therefore the rounded outer corners as shown in FIG. 6 prevent hanging-up or snagging when electrode 18 is pushed into well 60 to engage Venturi tube 48. Venturi tube 48 is preferably an elongated tube of brass, copper or steel, which is electrically conductive at least on the exterior surface thereof, and preferably is gold plated so corrosion will not occur and the high or higher electrical conductivity provided by the plating over the base or substrate material (brass) will remain over a long period of time.

Figure 9:
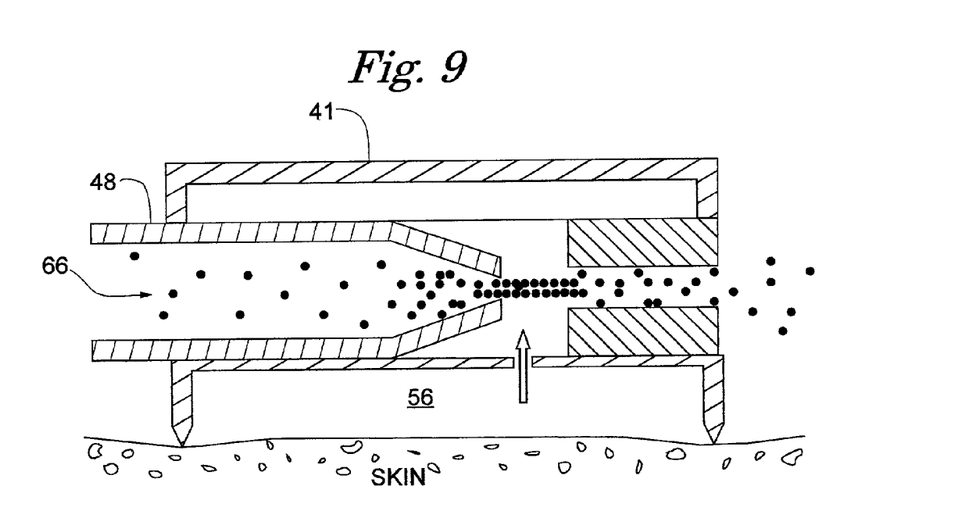
FIG. 9 is a cut away profile view of a Venturi tube in a preferred embodiment of the present invention.

With reference to FIG. 9, Venturi tube 48 has an internal Venturi arrangement with a suction port 66 positioned such that when fast moving or high-pressure gas (e.g., air) is passed through Venturi tube 48, a low-pressure constant vacuum is created in recess 56 of housing 41. It is the uniformity of each suction port 66 in each Venturi tube 48, which allows the clinician to disregard the pump during the ECG process. Such a vacuum in recess 56 is capable of allowing tissue to engage rim 42, bring the tissue into contact with electrode plate 44 to establish electrically conductive contact with the tissue. The vacuum also holds contactor 44 stationary against the tissue regardless of orientation, i.e., vertical, up-side-down, with this good holding power aided by the fact contactor 44 is light in weight. Venturi tube 48 is electrically conductive from electrode legs 45 to threaded end 49 of the tube 48. The threaded end 49 is exposed for connection to electrode hose 20, which also includes an output lead wire 64. The lead wire 64 is connected to a conductive threaded end of electrode hose 20, which connects at end 49 to the Venturi tube 48.

Therefore the patient's tissue is electrically connected through electrode plate 44 to electrode legs 45 to Venturi tube 48 to threaded end 49, to the lead wire 64 in electrode hose 20. Venturi tube 48 fits tightly into passage 61 of housing 41, and includes one or more collars 63 shown in FIG. 7 to aid in stabilizing the tube relative to the housing.

Figure 10:
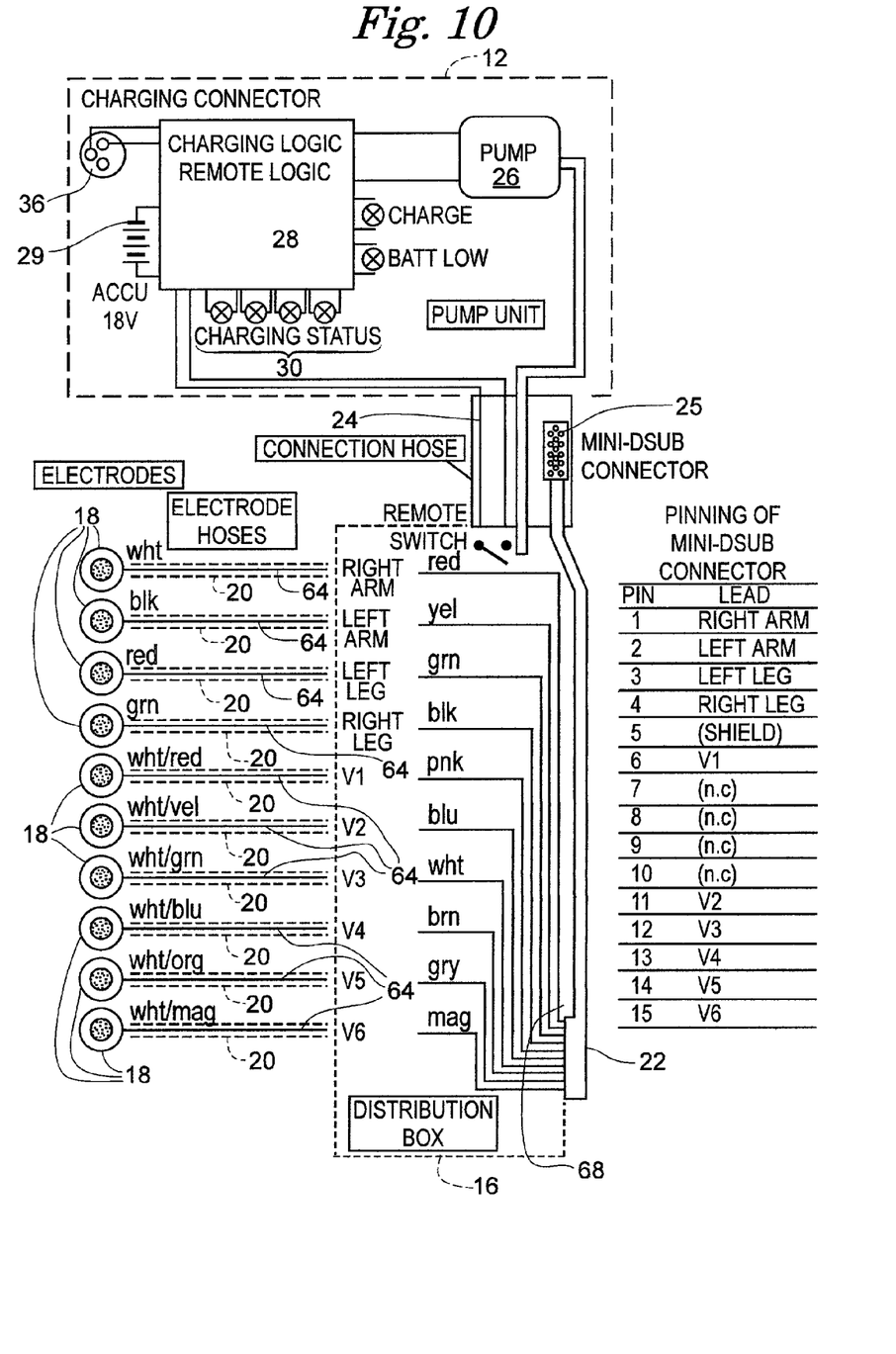
FIG. 10 is a schematic view of the electrical and pneumatic distribution in a preferred embodiment of the present invention.

With reference to FIG. 10, an electrical and pneumatic diagram is shown of a preferred embodiment of the present invention. From the Figure it can be shown that each electrode hose 20 has a lead wire 64 that travels inside the length of electrode hose 20. However, lead wire 64 is small relative to hose 20 and therefore allows enough room for pressurized air to travel to electrode 18. With reference to FIG. 2, the opposite end of electrode hose 20 is detachably connected to one of a plurality of apertures 66 located on distribution box 16. With reference once again to FIG. 10, when electrode hose 20 is plugged into aperture 66, lead wire 64 is electrically connected to connection wires 68, which travel down the center of connection hose 22. When connection hose 22 is detachably connected to combination plug 24 recorder connectors 68 are electrically connected to 15-pin mini-DSub connection 25. From here an outside connection cable can be plugged into D-Sub connector 25 at combination plug 24 and the other end plugged into any ECG recorder or monitor. DSub connection 25 allows for any recorder/monitor to be plugged in ECG electrode system 10.

Similar to lead wires 64, connection wires 68 are small relative to the size of connection hose 22 and therefore pressurized air can pass from pump unit 12 to distribution box 16. Further, with respect to FIG. 2, the pneumatic connection between pump 26, combination plug 24, and distribution box 16 can be seen. Pump 26 supplies pressurized air through air hose 38, then through air aperture 34, to combination plug 24, which will route pressurized air through to connection hose 22, which will then route pressurized air to distribution box 16, which routes the air to electrode hose 20, which then routes the pressurized air to electrode 18, which then expels the pressurized air through output port 47.

Figure 11:
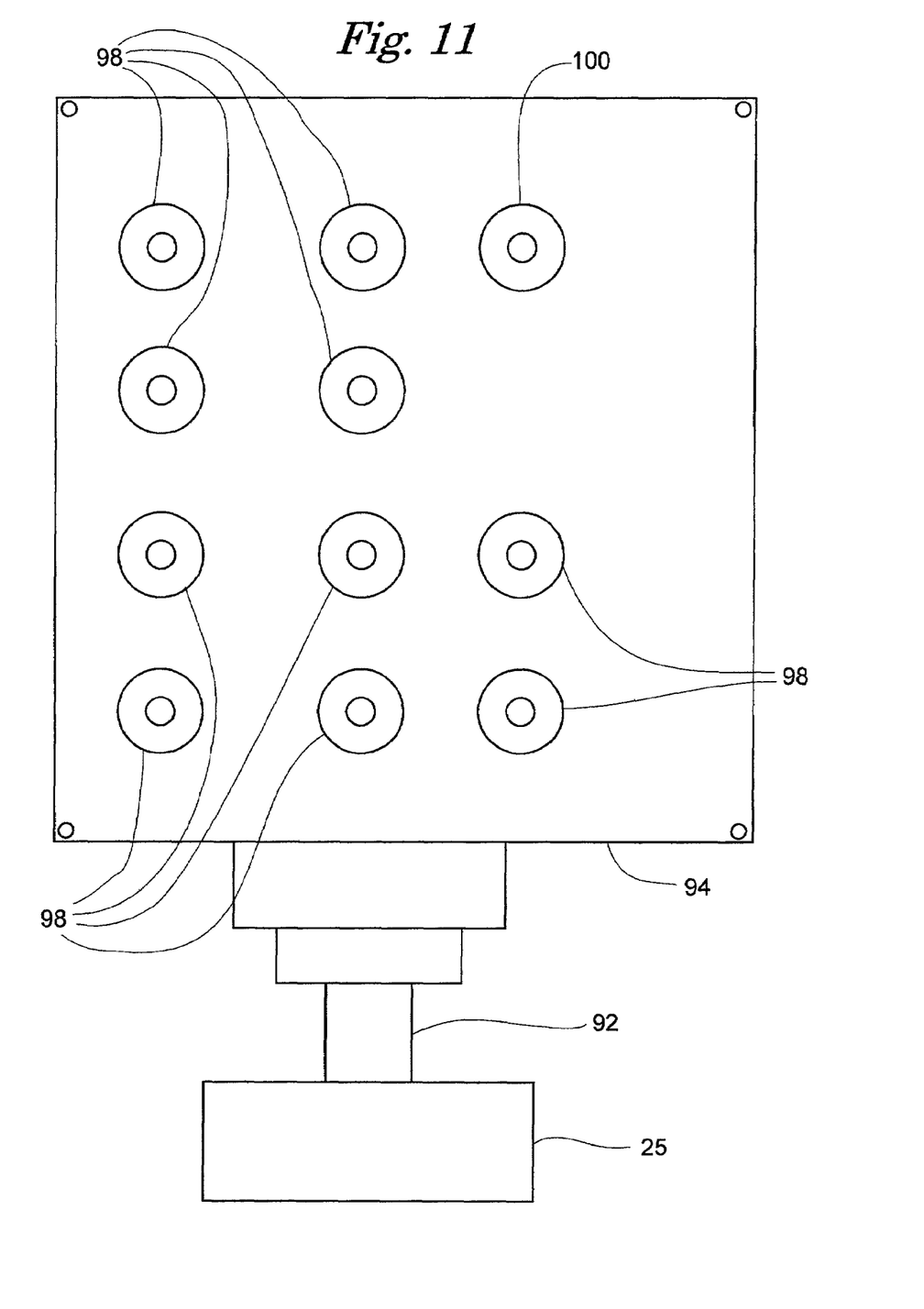
FIG. 11 is a front perspective view of the connection between the DSub connector and the jack box.

With reference to FIG. 11, DSub connection 25 allows for any analog recorder/monitor to be directly connected to ECG electrode system 10 of the present invention. Because the signal from electrodes 18 is never digitized, the signal can be sent directly to an analog recorder/monitor where the signal can be displayed. In addition, jack box 94 can be connected to D-Sub connector 25 via cable connector 92 and route the various signals coming from electrodes 18 to several or one analog to digital converters. The analog to digital converters can then feed the digital signals that result to any digital ECG recorder or monitor. Thus system 10 is adaptable to be used with any analog or digital recorder/ monitor. It is further contemplated that jack box 94 could also have the analog to digital converters onboard, in which case the jack box would then route the digital signal to any digital ECG recorder/monitor. In a preferred embodiment, jack box 94 is connected to an acquisition module 96 (FIG. 12) of an ECG system, which can then digitize the analog signal and route the signal to any digital ECG recorder or monitor.

Figure 12:
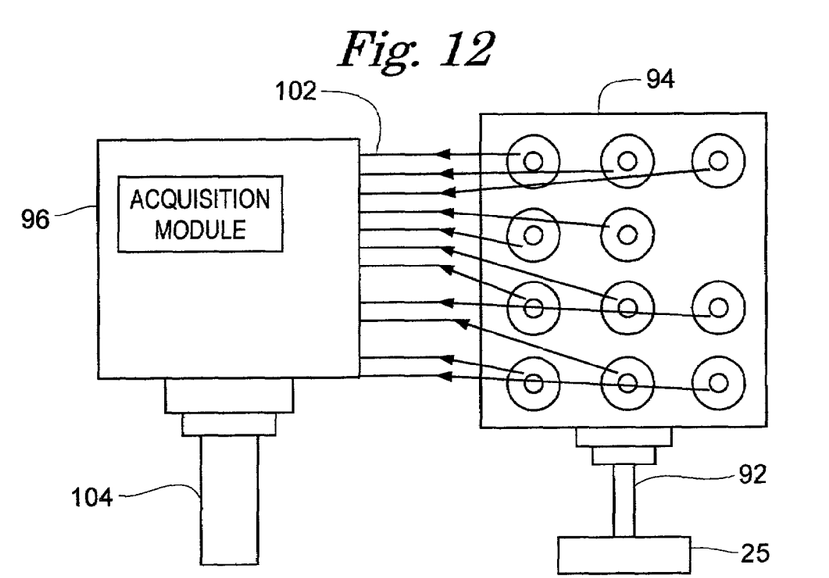
FIG. 12 is a front perspective view of the connection between the jack box of FIG. 11 and a typical acquisition module.

With further reference to FIG. 11, jack box 94 has 10 electrical input connections 98 and a ground connection 100 which are utilized to connect with any acquisition box 96 associated with an ECG system. Acquisition box 96 is implemented with ECG systems, which digitize the signals from the electrodes before routing these signals to an ECG recorder/monitor. With reference to FIG. 12, a schematic detailing the process of interconnecting jack box 94 to an acquisition box 96 of a standard ECG system is shown. The signals picked up by electrodes 18 and routed through to DSub connector 25, as discussed in detail above, are then routed through electrical connector 92, compatible with DSub connector 25, to jack box 94. Jack box 94 is then connected to acquisition box 96 via acquisition module conductors 102 which are plugged into jack box 94 via banana clips. Acquisition module 96 then digitizes the signal and routes the signal to a digital ECG recorder or monitor via electrical connection 104.

To activate ECG electrode system 10 the operator depresses remote activation switch 70 located at distribution box 16. As stated above, when control unit 28 receives the activation signal the microprocessor then initiates power from batteries 29 to pump 26. Pump 26 then relays compressed air through connection hose 22 to distribution unit 16 which directs the compressed air through electrode tubes 20 to the electrode to create a suction.

The operator then sprays an electrolytic solution of ionized water about six inches away from a location on a patient where the operator desires to place electrode 18. The operator should make sure that output port 47 remains unblocked, because this would stop the flow of air through electrode 18 and thus no vacuum would be created. The system typically avoids the need to shave the body portion, and instead the operator can typically apply an increased amount of solution and then press down electrode 18 while moving it in a circular motion. Then by lifting their finger on and off the output port 47 the operator can verify that electrode 18 is securely fixed to the patient. If the patient has large breasts, for instance, the operator would simply rotate electrode 18 45° to 90° from vertical so that output port 47 is not covered by the resting breast. The operator would have to remember that loose tissue would close output port 47 and cause limited or no suction to the patient. Because of the uniform suction created by pump 26, all electrodes 18 attach very quickly. Typically an operator could attach all ten electrodes 18 in less than 15 seconds.

Therefore, the operator does not have to shave the patient and thus the risk of infection is lowered and patient comfort is increased. Further, because of the quick adhesion of electrodes 18 the operator is able to begin and finish the ECG monitoring in a matter of minutes, therefore, labor cost is reduced. Finally, because an ionized water solution is used, clean up can be completed with a quick swipe of a paper towel and in some situations the ionized water simply evaporates and if the patient is sweaty then no ionized water needs to be applied because of the salt in the sweat is a good electrical conductor.

After the examination is completed the operator simply switches off ECG electrode system 10 by pressing remote switch 70 at distribution box 16. All electrodes 18 will then detach instantly. The operator then stows electrodes 18 and electrode hoses 20 in a safe and dry place to prevent contamination. The operator should avoid any contact between electrode contact plates 44 and metallic materials to reduce the possibility of chipping the silver/silver-chloride coating on contact plate 44 and reducing the electric conductivity of plate 44.

As discussed above, depending on the duration of each examination typically after 40–50 examinations batteries 29 will start to loose its charge. When this occurs control unit 28 will use indicator lights 30 and an audible alarm will sound to inform the clinician that use of battery charger 14 is necessary. Indicator lights 30 are visible at all times and reflect the current level of power available. Indicator lights 30 are divided into 6 groups:

| Currently charging | CHARGE |
| --- | --- |
| Full charge | 100% |
| 3/4 charge | 75% |
| 1/2 charge | 50 |
| 1/4 charge | 25 |
| Below 1/4 charge (Batteries Low) | <25 |

In addition a 10 second audible beep will sound and the<25% light will activate each time the unit is turned on. This indicates that the batteries 29 need to be recharged. It is of note, that more ECGs can be performed in this state; however, the reliability of the electrode suction will be reduced with every examination beyond this point. Therefore, when batteries 29 do need charging the user simply has to plug charger plug 40 into charger jack 36 and then plug main plug 42 into a wall outlet. It is of note that system 10 can not operate during the battery charging operation in order to prevent any possible harm to the patient or any faulty readings by system 10.

After an examination is completed the clinician need simply switch off system 10 by pressing remote switch 70 at distribution box 16. All electrodes 18 will detach immediately after loss of airflow.

The Venturi principle makes cleaning ECG electrode system 10 very easy. The operator simply switches on the system 10 by remote switch 70 and then hangs electrodes 18 in a vessel of water completely immersed. The operator then allows electrodes 18 to rest in the water for one to two minutes. When the operator removes electrodes 18 from the water the operator should let system 10 run for three minutes to allow electrodes 18 to air dry. This leaves the operator time to attend to other duties while drying occurs.

It will be appreciated that the present invention can take many forms and embodiments. The true essence and spirit of this invention are defined in the appended claims, and it is not intended that the embodiment of the invention presented herein should limit the scope thereof.

What is claimed is:

1. An ECG electrode system comprising:
  (a) an air pump for providing positively pressurized air through an exit orifice, (b) a flexible air connection hose having first and second ends, the first end of the hose being operably and detachably connected, or connectable, to the exit orifice of the pump, (c) an air distribution unit comprising a plurality of exit apertures and associated connectors, and an intake aperture and associated connector, the intake connector being detachably connected, or connectable, to the second end of the connection hose in order to controllably route pressurized air received from the pump, through the connection hose, and to the exit apertures, (d) a plurality of electrode tubes each comprising first and second ends, the first ends of each being operably and detachably connected, or connectable, to a corresponding distribution unit exit aperture, (e) a plurality of Venturi electrodes, each being operably and detachably connected, or connectable, to the second ends of the electrode tubes receiving compressed air from the electrode tubes, and (f) a plurality of electrical leads adapted to sense and relay electrical charges occurring within the body by means of a centralized universal electrical connector which is connectively compatible with one or more ECG recorders and monitors, wherein the electrode leads are each positioned within respective air connections hoses, in a manner sufficient to both protect the leads themselves and facilitate their positioning, wherein the housing includes a charging aperture adapted to receive a battery-charging unit.

2. A system according to claim 1 wherein the housing includes at least one LED to indicate the charge remaining in the battery.

3. A system according to claim 2 wherein the housing has at least one LED to indicate the status of the battery during charging of the battery.

4. A system according to claim 2 wherein the charging aperture is detachably connectable to a charging plug attached to the battery-charger.

5. A system according to claim 4 wherein the battery-charger provides a charge to the battery when the battery charger is detachably connected to a power supply.

6. An ECG electrode system comprising:
(a) an air pump for providing positively pressurized air through an exit orifice,
(b) a flexible air connection hose having first and second ends, the first end of the hose being operably and detachably connected, or connectable, to the exit orifice of the pump,
(c) an air distribution unit comprising a plurality of exit apertures and associated connectors, and an intake aperture and associated connector, the intake connector being detachably connected, or connectable, to the second end of the connection hose in order to controllably route pressurized air received from the pump, through the connection hose, and to the exit apertures,
(d) a plurality of electrode tubes each comprising first and second ends, the first ends of each being operably and detachably connected, or connectable, to a corresponding distribution unit exit aperture,
(e) a plurality of Venturi electrodes, each being operably and detachably connected, or connectable, to the second ends of the electrode tubes receiving compressed air from the electrode tubes, and
(f) a plurality of electrical leads adapted to sense and relay electrical charges occurring within the body by means of a centralized universal electrical connector which is connectively compatible with one or more ECG recorders and monitors, wherein the connection hose is detachably connected to a combination plug comprising a D-Sub connector adapted to permit an outside connection cable to be connected to an analog recorder/monitor, and to a jack box adapted to route signals from the electrodes to one or more analog or digital converters.

7. An ECG electrode system comprising:
(a) an air pump for providing positively pressurized air through an exit orifice,
(b) a flexible air connection hose having first and second ends, the first end of the hose being operably and detachably connected, or connectable, to the exit orifice of the pump,
(c) an air distribution unit comprising a plurality of exit apertures and associated connectors, and an intake aperture and associated connector, the intake connector being detachably connected, or connectable, to the second end of the connection hose in order to controllably route pressurized air received from the pump, through the connection hose, and to the exit apertures,
(d) a plurality of electrode tubes each comprising first and second ends, the first ends of each being operably and detachably connected, or connectable, to a corresponding distribution unit exit aperture,
(e) a plurality of Venturi electrodes, each being operably and detachably connected, or connectable, to the second ends of the electrode tubes receiving compressed air from the electrode tubes, and
(f) a plurality of electrical leads adapted to sense and relay electrical charges occurring within the body by means of a centralized universal electrical connector which is connectively compatible with one or more ECG recorders and monitors, and wherein the system further comprises a secondary electrode stabilization component adapted to stabilize the electrodes in the course of stress testing.

8. A system according to claim 7 wherein the secondary component comprises a lightweight mesh vest.

9. A method of performing ECG monitoring, the method comprising the steps of providing an ECG electrode system comprising:
(a) an air pump for providing positively pressurized air through an exit orifice,
(b) a flexible air connection hose having first and second ends, the first end of the hose being operably and detachably connected, or connectable, to the exit orifice of the pump,
(c) an air distribution unit comprising a plurality of exit apertures and associated connectors, and an intake aperture and associated connector, the intake connector being detachably connected, or connectable, to the second end of the connection hose in order to controllably route pressurized air received from the pump, through the connection hose, and to the exit apertures,
(d) a plurality of electrode tubes each comprising first and second ends, the first ends of each being operably and detachably connected, or connectable, to a corresponding distribution unit exit aperture,
(e) a plurality of Venturi electrodes, each being operably and detachably connected, or connectable, to the second ends of the electrode tubes receiving compressed air from the electrode tubes, and
(f) a plurality of electrical leads adapted to sense and relay electrical charges occurring within the body by means of a centralized universal electrical connector which is connectively compatible with one or more ECG recorders and monitors and attaching the electrodes to the body of a patient, wherein the electrode leads are each positioned within respective air connections hoses, in a manner sufficient to both protect the leads themselves and facilitate their positioning, and wherein the housing includes a charging aperture adapted to receive a battery-charging unit.

10. A method according to claim 9 wherein the housing includes at least one LED to indicate the charge remaining in the battery.

11. A method according to claim 10 wherein the housing has at least one LED to indicate the status of the battery during charging of the battery.

12. A method according to claim 10 wherein the charging aperture is detachably connectable to a charging plug attached to the battery-charger.

13. A method according to claim 12 wherein the battery-charger provides a charge to the battery when the battery charger is detachably connected to a power supply.

14. A method of performing ECG monitoring, the method comprising the steps of providing an ECG electrode system comprising:
(a) an air pump for providing positively pressurized air through an exit orifice,
(b) a flexible air connection hose having first and second ends, the first end of the hose being operably and detachably connected, or connectable, to the exit orifice of the pump,
(c) an air distribution unit comprising a plurality of exit apertures and associated connectors, and an intake aperture and associated connector, the intake connector being detachably connected, or connectable, to the second end of the connection hose in order to controllably route pressurized air received from the pump, through the connection hose, and to the exit apertures,
(d) a plurality of electrode tubes each comprising first and second ends, the first ends of each being operably and detachably connected, or connectable, to a corresponding distribution unit exit aperture,
(e) a plurality of Venturi electrodes, each being operably and detachably connected, or connectable, to the second ends of the electrode tubes receiving compressed air from the electrode tubes, and
(f) a plurality of electrical leads adapted to sense and relay electrical charges occurring within the body by means of a centralized universal electrical connector which is connectively compatible with one or more ECG recorders and monitors and attaching the electrodes to the body of a patient, wherein the connection hose is detachably connected to a combination plug comprising a D-Sub connector adapted to permit an outside connection cable to be connected to an analog recorder/monitor, and to a jack box adapted to route signals from the electrodes to one or more analog or digital converters.

15. A method of performing ECG monitoring, the method comprising the steps of providing an ECG electrode system comprising:
(a) an air pump for providing positively pressurized air through an exit orifice,
(b) a flexible air connection hose having first and second ends, the first end of the hose being operably and detachably connected, or connectable, to the exit orifice of the pump,
(c) an air distribution unit comprising a plurality of exit apertures and associated connectors, and an intake aperture and associated connector, the intake connector being detachably connected, or connectable, to the second end of the connection hose in order to controllably route pressurized air received from the pump, through the connection hose, and to the exit apertures,
(d) a plurality of electrode tubes each comprising first and second ends, the first ends of each being operably and detachably connected, or connectable, to a corresponding distribution unit exit aperture,
(e) a plurality of Venturi electrodes, each being operably and detachably connected, or connectable, to the second ends of the electrode tubes receiving compressed air from the electrode tubes, and
(f) a plurality of electrical leads adapted to sense and relay electrical charges occurring within the body by means of a centralized universal electrical connector which is connectively compatible with one or more ECG recorders and monitors, and attaching the electrodes to the body of a patient, wherein the system further comprises a secondary electrode stabilization component adapted to stabilize the electrodes in the course of stress testing.

16. A method according to claim 15 wherein the secondary component comprises a lightweight mesh vest.

* * * * *